United States Patent [19]

Wuest et al.

[11] Patent Number: 4,804,670
[45] Date of Patent: Feb. 14, 1989

[54] SUBSTITUTED HEXATRIENE DERIVATIVES AND THEIR USE IN TREATING ACNE AND PSORIASIS

[75] Inventors: Hans-Heiner Wuest, Dossenheim; Fritz-Frieder Frickel, Deidesheim; Joachim Paust, Neuhofen; Klaus Schmieder, Schortens; Axel Nuerrenbach, Gruenstadt, all of Fed. Rep. of Germany

[73] Assignee: BASF Aktiengesellschaft, Ludwigshafen, Fed. Rep. of Germany

[21] Appl. No.: 771,885

[22] Filed: Sep. 3, 1985

[51] Int. Cl.⁴ .................. A61K 31/41; A61K 31/19; C07D 257/04; C07C 63/04
[52] U.S. Cl. ..................... 514/381; 514/544; 514/570; 560/64; 562/405; 548/250; 548/237; 558/441; 564/336; 544/410
[58] Field of Search ............... 548/250; 514/381, 570, 514/544; 562/405; 560/64

[56] References Cited

U.S. PATENT DOCUMENTS 4,532,343 7/1985 Dawson et al. .................. 562/405

OTHER PUBLICATIONS

Richard Moon, The Retinoids, vol. 2, "Retinoids and Cancer", pp. 327-371, Academic Press, 1984.
Marcia I. Dawson, Journal Med. Chem. (1984), "Conformationally Restricted Retinoids", pp. 1516-1531.

Primary Examiner—David B. Springer
Attorney, Agent, or Firm—Keil & Weinkauf

[57] ABSTRACT

Substituted hexatriene derivatives of the formula I

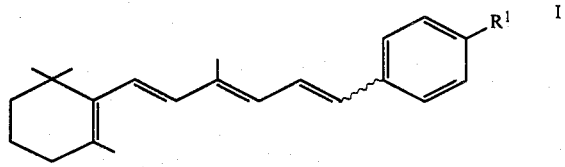

where $R^1$ has the meaning given in the description, and their preparation, are described. The compounds may be used to treat acne and psoriasis.

11 Claims, No Drawings

SUBSTITUTED HEXATRIENE DERIVATIVES AND THEIR USE IN TREATING ACNE AND PSORIASIS

The invention relates to novel hexatriene derivatives, to processes for their preparation and to their use in the treatment of illnesses.

It is known that polyene compounds, eg. retinol or retinoic acid, and also compounds in which one or more aromatic rings are incorporated into the polyene structure, exhibit pharmacological effects in the topical and systemic therapy of neoplasias and dermatoses, eg. acne or psoriasis (R. C. Moon and L. M. Hri in The Retinoids (Ed. M. B. Sporn, A. B. Roberts and D. S. Goodman), Vol. 2, p. 327 et seq., Academic Press, Inc. 1984; G. L. Peck, ibid. Vol. 2, p. 391 et seq.).

We have found that substituted hexatriene derivatives of the formula I

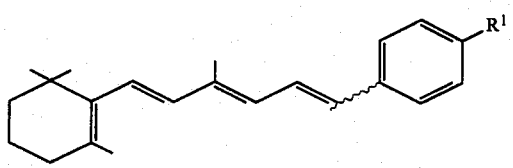

where $R^1$ is methyl, nitrile, $C_2$–$C_{10}$-ketal, oxazolinyl, tetrazolyl, —$CH_2OR^2$, —$CH_2NR^3R^4$ or —$COR^5$, where $R^2$ is hydrogen, $C_{1-4}$-alkyl, $C_{1-20}$-alkanoyl or unsubstituted benzoyl or benzoyl substituted by methyl, methoxy, halogen or nitro, $R^3$ and $R^4$ are hydrogen, $C_{1-4}$-alkyl, $C_{1-6}$-alkanoyl or unsubstituted benzoyl or benzoyl substituted by methyl, methoxy, halogen or nitro or together with the nitrogen atom to which they are bonded form a heterocyclic radical and —

$R^5$ is hydrogen, $C_{1-4}$-alkyl, halogen, —$OR^6$ or —$NR^7R^8$, where $R^6$ is hydrogen, unsubstituted or hydroxyl-substituted $C_{1-6}$-alkyl, unsubstituted or substituted aryl, or aralkyl which is unsubstituted or substituted in the aryl moiety and $R^7$ and $R^8$ are hydrogen, unsubstituted or hydroxyl-substituted $C_{1-6}$-alkyl, unsubstituted or substituted aryl, or aralkyl which is unsubstituted or substituted in the aryl moiety, or together with the nitrogen atom to which they are bonded form a heterocyclic radical, and, where relevant, their physiologically tolerated salts, exhibit improved action, especially in respect of the therapeutic index.

$R^1$ is preferably COOH.

$R^6$, $R^7$ and $R^8$ as aryl are preferably phenyl, which may be substituted by methyl, methoxy or nitro; $R^6$, $R^7$ and $R^8$ as aralkyl are preferably benzyl, which may be substituted by methyl, methoxy or halogen in the aryl moiety. $R^3$ and $R^4$, or $R^7$ and $R^8$, as heterocyclic radicals are preferably pyrrolidino, piperidino or morpholino. Preferred halogen atoms $R^5$ are fluorine and chlorine.

The 1E compounds are preferred to the 1Z compounds.

Typical examples of compounds according to the invention are: (all-E)-1-(4-carboxyphenyl)-4-methyl-6-2,6,6-trimethyl-1-cyclohexen-1-yl)-1,3,5-hexatriene, (all-E)-1-(4-carbomethoxyphenyl)-4-methyl-6-(2,6,6-trimethyl-1-cyclohexene-1-yl)-1,3,5-hexatriene, (all-E)-1-(4-carbethoxyphenyl)-4-methyl-6-(2,6,6-trimethyl-1-cyclohexen-1-yl)-1,3,5-hexatriene, (all-E)-1-(4-carbopropoxyphenyl)-4-methyl-6-(2,6,6-trimethyl-1-cyclohexene-1-yl)-1,3,5-hexatriene, (all-E)-1-(4-carbobutoxyphenyl)-4-methyl-6-(2,6,6-trimethyl-1-cyclohexene-1-yl)-1,3,5-hexatriene, (all-E)-1-(4-cyanophenyl)-4-methyl-6-(2,6,6-trimethyl-1-cyclohexen-1-yl)-1,3,5-hexatriene, (all-E)-1-(4-fluorocarbonylphenyl)-4-methyl-6-(2,6,6-trimethyl-1-cyclohexen-1-yl)-1,3,5-hexatriene, (all-E)-1-(4-chlorocarbonylphenyl)-4-methyl-6-(2,6,6-trimethyl-1-cyclohexen-1-yl)-1,3,5-hexatriene, (all-E)-1-(4-carbamylphenyl)-4-methyl-6-(2,6,6-trimethyl-1-cyclohexen-1-yl)-1,3,5-hexatriene, (all-E)-1-[4-(butylcarbamyl)phenyl]-4-methyl-6-(2,6,6-trimethyl-1-cyclohexene-1-yl)-1,3,5-hexatriene, (all-E)-1-[4-(diethylcarbamyl)phenyl]-4-methyl-6-(2,6,6-trimethyl-1-cyclohexen-1-yl)-1,3,5-hexatriene, (all-E)-1-[4-(2-hydroxyethylcarbamyl)phenyl]-4-methyl-6-(2,6,6-trimethyl-1-cyclohexen-1-yl)-1,3,5-hexatriene, (all-E)-1-[4-(phenylcarbamyl)phenyl]-4-methyl-6-(2,6,6-trimethyl-1-cyclohexen-1-yl)-1,3,5-hexatriene, (all-E)-1-[4-(benzylcarbamyl)phenyl]-4-methyl-6-(2,6,6-trimethyl-1-cyclohexen-1-yl)-1,3,5-hexatriene, (all-E)-1-[4-(morpholinocarbamyl)phenyl]-4-methyl-6-(2,6,6-trimethyl-1-cyclohexen-1-yl)-1,3,5-hexatriene, (all-E)-1-(4-formylphenyl)-4-methyl-6-(2,6,6-trimethyl-1-cyclohexen-1-yl)-1,3,5-hexatriene, (all-E)-1-(4-acetylphenyl)-4-methyl-6-(2,6,6-trimethyl-1-cyclohexen-1-yl)-1,3,5-hexatriene, (all-E)-1-[4-(hydroxymethyl)phenyl]-4-methyl-6-(2,6,6-trimethyl-1-cyclohexen-1-yl)-1,3,5-hexatriene, (all-E)-1-[4-(methoxymethyl)phenyl]-4-methyl-6-(2,6,6-trimethyl-1-cyclohexen-1-yl)-1,3,5-hexatriene, (all-E)-1-[4-(phenoxymethyl)phenyl]-4-methyl-6-(2,6,6-trimethyl-1-cyclohexen-1-yl)-1,3,5-hexatriene, (all-E)-1-[4-(benzyloxymethyl)phenyl]-4-methyl-6-(2,6,6-trimethyl-1-cyclohexen-1-yl)-1,3,5-hexatriene, (all-E)-1-[4-(formyloxymethyl)phenyl]-4-methyl-6-(2,6,6-trimethyl-1-cyclohexen-1-yl)-1,3,5-hexatriene, (all-E)-1-[4-(acetoxymethyl)phenyl]-4-methyl-6-(2,6,6-trimethyl-1-cyclohexen-1-yl)-1,3,5-hexatriene, (all-E)-1-[4-(propionyloxymethyl)phenyl]-4-methyl-6-(2,6,6-trimethyl-1-cyclohexen-1-yl)-1,3,5-hexatriene, (all-E)-1-[4-(hexadecanoyloxymethyl)phenyl]-4-methyl-6-(2,6,6-trimethyl-1-cyclohexen-1-yl)-1,3,5-hexatriene, (all-E)-1-[4-(aminomethyl)phenyl]-4-methyl-6-(2,6,6-trimethyl-1-cyclohexen-1-yl)-1,3,5-hexatriene, (all-E)-1-[4-(N-methylaminomethyl)phenyl]-4-methyl-6-(2,6,6-trimethyl-1-cyclohexen-1-yl)-1,3,5-hexatriene, (all-E)-1-[4-(N,N-diethylaminomethyl)phenyl]-4-methyl-6-(2,6,6-trimethyl-1-cyclohexen-1-yl)-1,3,5-hexatriene, (all-E)-1-[4-(morpholinomethyl)phenyl]-4-methyl-6-(2,6,6-trimethyl-1-cyclohexen-1-yl)-1,3,5-hexatriene, (all-E)-1-[4-(pyrrolidinomethyl)phenyl]-4-methyl-6-(2,6,6-trimethyl-1-cyclohexen-1-yl)-1,3,5-hexatriene, (all-E)-1-[4-(piperidinomethyl)phenyl]-4-methyl-6-(2,6,6-trimethyl-1-cyclohexen-1-yl)-1,3,5-hexatriene, (all-E)-1-[4-(N-formylaminomethyl)phenyl]-4-methyl-6-(2,6,6-trimethyl-1-cyclohexen-1-yl)-1,3,5-hexatriene, (all-E)-1-[4-(N-acetylaminomethyl)phenyl]-2,6,6-trimethyl-1-cyclohexen-1-yl)-1,3,5-hexatriene, (all-E)-1-[4-(N-benzoylaminomethyl)phenyl]-4-methyl-6-(2,6,6-trimethyl-1-cyclohexen-1-yl)-1,3,5-hexatriene, (all-E)-1-[4-(dioxolan-2-yl)phenyl]-4-methyl-6-(2,6,6-trimethyl-1-cyclohexen-1-yl)-1,3,5-hexatriene, (all-E)-1-[4-(oxazolin-2-yl)phenyl]-4-methyl-6-(2,6,6-trimethyl-1-cyclohexen-1-yl)-1,3,5-hexatriene, (all-E)-1-[4-(tetrazol- 5-yl)phenyl]-4-methyl-6-(2,6,6-trimethyl-1-cyclohexen-1-yl)-1,3,5-hexatriene, (1Z,3E,5E)-1-(4-carboxyphenyl)-4-methyl-6-(2,6,6-trimethyl-1-cyclohexen-1-yl)-1,3,5-hexatriene, (1Z,3E,5E)-1-(4-carbomethoxyphenyl)-4-methyl-6-(2,6,6-trimethyl-1-cyclohexen-1-yl)-1,3,5-hexatriene, (1Z,3E,5E)-1-(4-carbethoxyphenyl)-4-methyl-6-(2,6,6-trimethyl-1-cyclohexen-1-yl)-1,3,5-hexatriene and (1Z,3E,5E)-1-(4-cyanophenyl)-4-methyl-6-(2,6,6-trimethyl-1-cyclohexen-1-yl)-1,3,5-hexatriene.

The compounds according to the invention may be prepared by a method wherein a phosphonium salt of the formula II

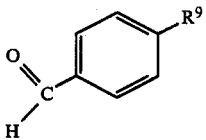

where $X^\ominus$ is an anion, eg. chloride, bromide or, preferably, bisulfate, is reacted with an aromatic aldehyde of the formula III

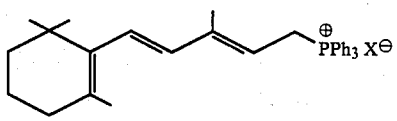

where $R^9$ is methyl, nitrile or $-COOR^{10}$, and $R^{10}$ is hydrogen or $C_{1-3}$-alkyl, in a Wittig reaction. Advantageously, the process is carried out in a solvent in the presence of the basic compounds conventionally used for Wittig reactions.

The Wittig reaction takes place at a temperature of up to 100° C., advantageously at from 20° to 50° C. The reaction can be carried out under atmospheric pressure or in a closed vessel under superatmospheric pressure, if appropriate with heating to the stated temperature range.

This reaction can be carried out in the presence of a diluent or solvent, for example a lower saturated dialkyl ether, dialkyl glycol ether or cyclic ether, such as diethyl ether, ethyl tert.-butyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, eg. hexane, heptane or isooctane, a lower aliphatic ketone, eg. acetone, methyl ethyl ketone or methyl isobutyl ketone, a dialkylformamide, eg. dimethylformamide or diethylformamide, or a mixture of the said solvents. The use of cyclic ethers, eg. dioxane or tetrahydrofuran, and especially of dimethylformamide or mixtures of these, is preferred, the reaction in general taking place at up to 30° C.

The reactions are carried out in the presence of a deprotonizing agent for the phosphonium salt II. Suitable agents are alkali metal hydrides and alkali metal amides, especially the sodium and potassium compounds, as well as the sodium and potassium salts of dimethylsulfoxide, alkyl-lithium compounds, eg. n-butyl-lithium, and alkali metal alcoholates, preferably sodium methanolate and sodium ethanolate.

The compounds according to the invention can also be obtained by the Wittig-Horner type of reaction, wherein the aldehyde IV

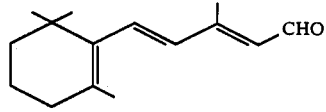

is reacted with a phosphonate of the formula V

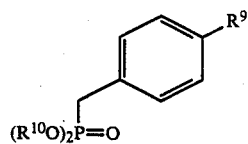

where $R^9$ has the above meaning and $R^{10}$ is $C_{1-4}$-alkyl. These reactions proceed similarly to the above-described Wittig reactions in the presence of a suitable deprotonizing agent.

The Wittig reaction or Wittig-Horner reaction usually gives a mixture of the stereoisomeric (E/Z) olefins.

E/Z isomer mixtures in which the Z-compound predominates undergo rearrangement at the olefinic double bond, under the action of light, to give mixtures with a higher proportion of the E isomers. Pure E compounds of the formula (I) can advantageously be obtained from the E/Z isomer mixtures resulting from the rearrangement, which now have an increased content of the E compound, preferably by crystallization or by a chromatographic method such as column chromatography or preparative HPL chromatography.

The photoisomerization is preferably carried out in solution. Suitable solvents are polar protic or aprotic solvents, eg. methanol, ethanol, ethyl acetate, tetrahydrofuran and acetone. The concentration of the irradiated solution is from 0.1 to 50, preferably from 1 to 15 percent by weight.

The irradiation can be carried out in the presence of a sensitizer, for example acetophenone, 4-methoxyacetophenone, propiophenone, benzene, acetone, benzophenone, benzil or Michler's ketone. Acetone is particularly preferred.

Light sources which may be used to carry out the said photoreaction are artificial sources, the emission of which lies at least partially in the range from 200 to 600 nm, preferably from 300 to 400 nm. Mercury vapor lamps, xenon lamps, tungsten lamps, fluorescent tubes or carbon arc lamps may advantageously be employed.

The irradiation temperature depends on the nature of the solvent used. The range from +10° to +30° C. is particularly preferred. The radiant heat can be removed by cooling the lamp and/or cooling the reaction mixture; distilled water or filtering solutions to which additives have been added in a known manner may be used in the lamp coolant circuit.

If desired, the benzoic acid esters of the general formula I are converted to the free carboxylic acids and their physiologically tolerated salts by ester hydrolysis. Conversely, the free acid can of course be esterified in a known manner.

Advantageously, the hydrolysis/esterification is carried out in the presence of a diluent or solvent, for example a dialkyl glycol ether or cyclic ether, eg. 1,2-dimethoxyethane, tetrahydrofuran or dioxane, a lower aliphatic ketone, eg. acetone, methyl ethyl ketone or methyl isobutyl ketone, or a lower aliphatic alcohol, eg.

methanol, ethanol, propanol or isopropanol, if appropriate in the presence of water, or in mixtures of the said solvents with water.

Preferred solvents are aqueous mixtures of ethanol and methanol, the reaction being carried out at the boiling point of the reaction mixture.

The hydrolysis is preferably carried out in the presence of an alkali, such as an alkali metal hydroxide, alkali metal carbonate or alkali metal bicarbonate, especially the compounds of sodium and potassium, a tertiary organic base, such as pyridine or a lower trialkylamine, eg. trimethylamine or triethylamine, mixed with water. A stoichiometric amount or slight excess of base, relative to the ester, is employed. The use of sodium hydroxide or potassium hydroxide is preferred.

The amides according to the invention can be prepared in a manner known per se, by first converting the corresponding benzoic acids into derivatives in which the carbonyl group is more active, for example into the acid halides, azides, imidazolides or anhydrides, the O-acyl-N,N'-dicyclohexylisoureas or p-nitrophenyl esters, and treating these with amines $HNR^7R^8$. In the case of particularly reactive amines, especially ammonia, direct amidolysis of esters (containing the radical $-OR^6$) is preferred.

A halide of a carboxylic acid, preferably the acid chloride, can be converted to an oxazoline derivative of the formula I by reaction with 2-aminoethanol and subsequent cyclization.

A carboxylic acid, a carboxylic acid ester or a carboxylic acid amide of the formula I can be reduced in a manner known per se to the corresponding alcohol or amine. Advantageously, the reduction is carried out with the aid of a metal hydride or alkali metal hydride in the presence of a suitable solvent. Preferred metal hydrides are complex compounds such as lithium aluminum hydride or diisobutyl-aluminum hydride. Solvents employed when working with lithium aluminum hydride are ethers, eg. diethyl ether, dioxane or tetrahydrofuran. If the reduction is carried out with diisobutyl-aluminum hydride or an alkoxy-sodium aluminum hydride, the use of hydrocarbons, eg. hexane or toluene, is preferred.

An amine or alcohol of the formula I can be converted to the amide or ester according to the invention in a manner known per se, by reaction with an alkanoyl halide or anhydride, an aralkyl halide or anhydride or an aroyl or heteroaroyl halide or anhydride, advantageously in an inert diluent or solvent, for example a lower aliphatic ketone such as acetone, methyl ethyl ketone or methyl isobutyl ketone, a dialkylformamide, such as dimethylformamide or diethylformamide, or an excess of the acylating agent as the diluent or solvent. Preferably, the reactions are carried out in the presence of a base as an acid acceptor, at between $-20°$ C. and the boiling point of the reaction mixture. Suitable bases are alkali metal carbonates, bicarbonates, hydroxides or alcoholates, especially those of sodium and potassium, basic oxides, eg. aluminum oxide or calcium oxide, organic tertiary bases, eg. pyridine, or lower trialkylamines, eg. trimethylamine or triethylamine. The bases can be employed in catalytic amount or in a stoichiometric amount or slight excess relative to the alkylating agent employed.

An alcohol of the formula I can be reacted with an alkyl halide $R^2$—I, $R^2$—Br or $R^2$—Cl in the presence of an alkali metal hydride, preferably sodium hydride, or in the presence of an alkyl-lithium compound, preferably n-butyl-lithium, in an organic solvent, such as tetrahydrofuran, dioxane, 1,2-dimethoxyethane, methyl tert.-butyl ether or, when using sodium hydride, also in dimethylformamide, at from $-10°$ C. to 40° C., to give an ether of the formula I.

An alcohol of the formula I can be oxidized with suitable oxidizing agents, preferably manganese(IV) oxide, if desired on an inorganic carrier such as silica gel or aluminum oxide, to give an aldehyde of the formula I. Advantageously, the reaction is carried out in an inert organic solvent, for example a hydrocarbon, eg. hexane, or an ether, eg. tetrahydrofuran, or in a mixture of the said solvents and diluents, at from $-10°$ C. to 30° C. The required reaction time essentially depends on the oxidation activity of the manganese(IV) oxide employed.

An aldehyde of the formula I can also be obtained by reducing the corresponding nitrile of the formula I with diisobutyl-aluminum hydride in a solvent, preferably in toluene, hexane, tetrahydrofuran or a mixture of these solvents, at from $-40°$ C. to room temperature.

A nitrile of the formula I can be hydrolyzed in a manner known per se, using acid catalysis or, more advantageously, base catalysis, to give the corresponding carboxylic acid. Preferred bases are alkali metal hydroxides, especially potassium hydroxide, which is employed in excess. The solvents employed are, as a rule, water-miscible alcohols, eg. methanol, ethanol, isopropanol or n-butanol. The reaction is usually carried out at the boiling point of the reaction mixture.

The nitriles of the formula I can be converted to the corresponding tetrazoles of the formula I by addition reaction with an azide, for example an alkali metal azide, preferably sodium azide, in the presence of aluminum chloride or ammonium chloride. The solvents used are preferably cyclic ethers, such as dioxane or tetrahydrofuran, and, in particular, dimethylformamide, or mixtures of these, and the reaction is in general carried out at from 60° to 100° C.

Some of the compounds according to the invention have an acidic hydrogen atom and can therefore be converted in the conventional manner, by means of a base, into a physiologically tolerated, readily water-soluble salt. Examples of suitable salts are ammonium salts, alkali metal salts, especially those of sodium, potassium and lithium, alkaline earth metal salts, especially those of calcium or magnesium, and salts with suitable organic bases, such as with lower alkylamines, for example methylamine, ethylamine or cyclohexylamine, or with substituted lower alkylamines, especially hydroxy-substituted alkylamines, eg. diethanolamine, triethanolamine or tris-(hydroxymethyl)-aminomethane, as well as with piperidine or morpholine.

If desired, the novel amines obtained, of the formula (I), are converted by conventional methods to acid addition salts with physiologically tolerated acids. Examples of conventional physiologically tolerated inorganic acids are hydrochloric acid, hydrobromic acid, phosphoric acid and sulfuric acid, while examples of physiologically tolerated organic acids are oxalic acid, maleic acid, fumaric acid, lactic acid, tartaric acid, malic acid, citric acid, salicylic acid, adipic acid and benzoic acid; further suitable acids may be found in Fortschritte der Arzneimittelforschung, 10, 224–225, Birkhäuser Verlag, Basle and Stuttgart, 1966.

Because of their pharmacological properties the novel compounds and their physiologically tolerated salts may be employed in the topical and systemic therapy of acne, psoriasis and other dermatological disorders associated with pathologically modified keratinization.

They may also be used for topical and systemic therapy, and for prophylaxis, of precanceroses and carcinomas of the skin, the mucous membranes and internal organs, as well as for the treatment of rheumatic disorders, especially disorders of an inflammatory or degenerative nature which affect the joints, muscles, sinews and other parts of the locomotor apparatus. A preferred field of indication, in addition to the therapy of dermatological disorders, is the prophylactic and therapeutic treatment of precanceroses and tumors.

The pharmacological effects can be demonstrated in, for example, the following test models:

The dermatological activity, for example in the treatment of acne, can be demonstrated, inter alia, through the comedolytic activity and the ability to reduce the number of cysts in the rhino-mouse model [L. H. Kligman et al., The Journal of Investigative Dermatology 73 (1978), 354-358, and J. A. Mezick et al. in Models of Dermatology (Ed. Maibach, Lowe), vol. 2, pages 59-63, Karger, Basel 1985].

The test substance in a suitable carrier was applied topically (100 μl) to the entire back area of the Rhino mouse, application being effected once a day on five successive days per week for two weeks. After 72 hours after the final treatment, the dorsal skin was removed, and left in 0.5% strength acetic acid for 18 hours at 4°-6° C. Thereafter, an area of about 2×5 cm² was cut out and the epidermis was peeled off, placed on a microscope slide (with the dermal side upward) and washed water-free with alcohol/xylene until the epidermis appeared transparent. The sample was fixed by coating it with Permount, and evaluated microscopically. The diameters of 10 utricles in 5 freely selected areas were measured in each case, and the mean reduction in the utricle diameter was calculated from this by comparison with the untreated control group. The Table below shows the results obtained.

TABLE

| Substance | Dose mg/ml | Reduction in the utricle diameter in % |
|---|---|---|
| Example 7 | 2 | 56.3 |
| Example 6 | 2 | 51.1 |
| Example 3 | 1 | 56.6 |
| | 0.1 | 26.6 |

The compounds according to the invention counteract the vitamin A deficiency-induced keratinization of hamster tracheal tissue in vitro. Keratinization is part of the early stage of carcinogenesis which, using a similar technique in vivo is inhibited by the compounds according to the invention, of the formula (I), after initiation by chemical compounds, by high energy radiation or by viral cell transformation (Cancer Res. 36 (1976), 964-972; Nature 250 (1974), 64-66; Nature 253 (1975), 47-50).

In addition, the compounds according to the invention inhibit the proliferation of certain cells which show malignant changes (J. Natl. Cancer Inst. 60 (1978), 1035-1041; Experimental Cell Research 117 (1978), 15-22; Proc. Natl. Acad. Sci. USA 77 (1980) 2837-2940).

The anti-arthritic action of the compounds according to the invention can be determined in the usual manner in an animal experiment, employing the adjuvant arthritis model.

Accordingly, the invention also relates to therapeutic compositions for topical and systemic use, which contain a compound of the formula (I) as the active substance, in addition to conventional carriers or diluents, and to the use of a compound of the formula (I) for the preparation of a drug.

The therapeutic compositions or formulations are prepared using the conventional liquid or solid carriers or diluents and the conventional pharmaceutical auxiliaries, in accordance with the desired administration route and employing a dose suitable for the particular application, the process being carried out in the conventional manner, for example by mixing the active substance with the solid or liquid carriers and auxiliaries conventionally used in such formulations.

The formulations can accordingly be administered perorally, parenterally or topically. Examples of such formulations are tablets, film tablets, coated tablets, capsules, pills, powders, solutions, suspensions, infusion solutions, injection solutions, pastes, ointments, jellies, creams, lotions, powders, solutions, emulsions and sprays.

The therapeutic formulations can contain the compounds to be used according to the invention in a concentration of from 0.001 to 1%, preferably from 0.001 to 0.1%, for local application and in an individual dose of, preferably, from 0.1 to 50 mg for systemic use and can be administered in one or more doses per day, depending on the nature and severity of the disorder.

Conventional pharmaceutical auxiliaries are, for example, alcohols, eg. isopropanol, oxyethylated castor oil or oxyethylated hydrogenated castor oil, polyacrylic acid, glycerol monostearate, medicinal paraffin, white petroleum jelly, lanolin, polyethylene glycol 400, polyethylene glycol 400 stearate and oxyethylated fatty alcohol for local use and lactose, propylene glycol, ethanol, starch, talc and polyvinylpyrrolidone for systemic use. Where appropriate, an antioxidant, for example tocopherol, butylated hydroxyanisole or butylated hydroxytoluene, or a flavor improver, stabilizer, emulsifier, lubricant etc. can be added to the formulation, with the proviso that all substances used in the preparation of the pharmaceutical formulation are toxicologically safe and compatible with the active compounds used. Preparation of the compounds according to the invention:

EXAMPLE 1

(all-E)-1-(4-Cyanophenyl)-4-methyl-6-(2,6,6-trimethyl-1-cyclohexen-1-yl)-1,3,5-hexatriene A solution of 7.8 g (0.34 mole) of sodium in 62 ml of methanol was added dropwise over 15 minutes, at from 0° to 5° C., to a solution of 116.8 g (0.2 mole) of -ionylidene-ethyltriphenylphosphonium bisulfate and 32.7 g (0.25 mole) of p-cyanobenzaldehyde in 0.5 liter of methanol. The mixture was stirred for a further 18 hours at room temperature, 100 ml of water were then added and insoluble constituents were filtered off. The filtrate was extracted five times with 300 ml of heptane/ether (5:1) at a time. The organic phase was dried (Na₂SO₄) and concentrated, leaving 521 g of solid substance. The latter was recrystallized from 200 ml of methanol+100 ml of ethanol and thereafter again from 300 ml of heptane. 15.1 g of crystalline product (E/Z=3:1) were thus obtained. On again recrystallizing the material from 75 ml of heptane, 10.2 g (16%) of the compound shown in the title were obtained as the pure isomer, of melting point 120°–121° C.

EXAMPLE 2

(all-E)- and (1Z,3E,5E)-1-(4-Carbethoxyphenyl)-4-methyl-6-(2,6,6-trimethyl-1-cyclohexen-1-yl)-1,3,5-hexatriene A solution of 6.3 g (0.275 mole) of sodium in 135 ml of absolute ethanol was added dropwise in the course of 25 minutes, at from 5° to 10° C., to a solution of 95.5 g (0.17 mole) of -ionylidene-ethyltriphenylphosphonium bisulfate and 37.4 g (0.21 mole) of ethyl p-formylbenzoate in 400 ml of absolute ethanol. The reaction mixture was stirred for a further 18 hours at room temperature and was then concentrated to one-quarter of its volume. 250 ml of heptane were added to the residue and the batch was mixed thoroughly. The heptane phase was then decanted and the entire process was repeated twice more. The combined heptane phases were washed three times with 250 ml of methanol/water (3:2) at a time, dried (Na$_2$SO$_4$) and concentrated. The residue was separated by means of preparative HPLC (silica gel 60, heptane+1% of ethyl acetate). The first fraction contained 12.8 g (21%) of the 1Z isomer of the compound shown in the title, as an oil. The second fraction consisted of 13.8 g of crystals which were stirred with 10 ml of ethanol and filtered off. This gave 3.4 g (11%) of the all-E isomer of the compound shown in the title, melting point 140°–141° C.

EXAMPLE 3

(all-E)-1-(4-Carboxyphenyl)-4-methyl-6-(2,6,6-trimethyl-1-cyclohexen-1-yl)-1,3,5-hexatriene (a) 4 g (12.6 millimole) of (all-E)-1-(4-cyanophenyl)-4-methyl-6-(2,6,6-trimethyl-1-cyclohexen-1-yl)-1,3,5-hexatriene from Example 1 in 60 ml of ethanol+40 ml of 10N sodium hydroxide solution were refluxed for 2 hours. The mixture was poured into water and acidified with concentrated hydrochloric acid. The precipitate was filtered off, washed neutral with water, rinsed with a small amount of methanol and dried. 4 g (94%) of slightly impure product of melting point 215° C. were obtained.

For further purification, the compound was recrystallized once from toluene/heptane and a second time from isopropanol. 2.6 g (61%) of the pure compound shown in the title were obtained. Melting point 218° C.

(b) 2.9 g (8 millimoles) of (all-E)-1-(4-carbethoxyphenyl)-4-methyl-6-(2,6,6-trimethyl-1-cyclohexen-1-yl)-1,3,5-hexatriene from Example 2, in a solution of 1.1 g of potassium hydroxide (85% pure) in 35 ml of ethanol were refluxed for 2.5 hours. When the mixture had cooled, it was poured into 0.5 liter of water and 50 ml of ethanol, the batch was acidified and stirred for a few minutes, and the precipitate formed was filtered off with suction, washed thoroughly with water and rinsed repeatedly with a small amount of ethanol. After drying, 2.6 g (97%) of the compound shown in the title remained, in the form of yellow crystals of melting point 219°–220° C.

EXAMPLE 4

(1Z,3E,5E)-1-(4-Carboxyphenyl)-4-methyl-6-(2,6,6-trimethyl-1-cyclohexen-1-yl)-1,3,5-hexatriene A solution of 15.6 g (0.68 mole) of sodium in 400 ml of absolute ethanol was added dropwise over 15 minutes at 15° C. to a solution of 112.4 g (0.2 mole) of -ionylidene-ethyltriphenylphosphonium bisulfate and 37.5 g (0.25 mole) of p-carboxybenzaldehyde in 500 ml of absolute ethanol. The mixture was stirred for a further 18 hours at room temperature and then poured into 1 liter of water, and the batch was acidified and extracted three times with 250 ml of ether at a time. The smeary residue which remained after the combined ether phases had been dried (Na$_2$SO$_4$) and concentrated was triturated with 400 ml of ethanol. The crystals were filtered off with suction and washed repeatedly with a total of 200 ml of acetone. Recrystallization from ethyl acetate gave 18.4 g (27%) of the compound shown in the title, melting point 179° C.

EXAMPLE 5

(all-E)-1-[4-(Tetrazol-5-yl)phenyl]-4-methyl-6-(2,6,6-trimethyl-1-cyclohexen-1-yl)-1,3,5-hexatriene 6.7 g (0.05 mole) of aluminum chloride were added cautiously, a little at a time, to a suspension of 13 g (0.2 mole) of sodium azide in 100 ml of tetrahydrofuran at 0° C. The mixture was refluxed for 45 minutes, 3.2 g (0.01 mole) of (all-E)-1-(4-cyanophenyl)-4-methyl-6-(2,6,6-trimethyl-1-cyclohexen-1-yl)-1,3,5-hexatriene from Example 1 were added and the batch was refluxed for a further 18 hours. The reaction mixture was then added to 0.7 liter of water, 200 ml of ethanol were added, and the whole was acidified. Upon prolonged stirring at room temperature, a solid formed and this was filtered off with suction and washed with ethanol/heptane (1:1). Upon drying, 2.6 g (72%) of the compound shown in the title were obtained; melting point 195°–196° C.

EXAMPLE 6

(all-E)-1-(4-Formylphenyl)-4-methyl-6-(2,6,6-trimethyl-1-cyclohexen-1-yl)-1,3,5-hexatriene A solution of 0.12 mole of diisobutyl-aluminum hydride in 100 ml of toluene was rapidly added dropwise to a solution of 19 g (0.06 mole) of (all-E)-1-(4-cyanophenyl)-4-methyl-6-(2,6,6-trimethyl-1-cyclohexen-1-yl)-1,3,5-hexatriene from Example 1 in a mixture of 250 ml of absolute ether and 50 ml of absolute tetrahydrofuran, with gentle cooling at 5°–10° C. Stirring was continued for 2 hours at room temperature and the mixture was then cautiously hydrolyzed with water and saturated tartaric acid solution. The batch was extracted 7 times with 200 ml of ether at a time and the combined ether phases were washed once with water, dried (Na$_2$SO$_4$) and concentrated. The residue (20 g of a dark brown oil) was purified by column chromatography (silica gel 60, 230–400 mesh, 180 g; heptane with increasing proportions of toluene). 11.1 g (58%) of the title compound were thus obtained, melting point 62°–63° C.

EXAMPLE 7

(all-E)-1-[4-(Hydroxymethyl)phenyl]-4-methyl-6-(2,6,6-trimethyl-1-cyclohexen-1-yl)-1,3,5-hexatriene 9.6 g (0.03 mole) of the aldehyde described in the above Example 6 were dissolved in 300 ml of isopropanol and a total of 2.3 g (0.06 mole) of sodium borohydride was added, a little at a time, at room temperature. Stirring was continued for 2 hours at room temperature and the mixture was then poured into 0.6 liter of water and extracted 3 times with 150 ml of ether at a time. The combined ether phases were washed once with saturated sodium chloride solution, dried (Na$_2$SO$_4$) and concentrated. The residue (8.7 g of oil) was purified by column chromatography (silica gel 60, 230-400 mesh; heptane with increasing proportions of ethyl acetate). The eluate was concentrated and then caused to crystallize by trituration. The solid (4.4 g) was thoroughly stirred with 15 ml of heptane, filtered off with suction and dried. 3.0 g (30%) of the title compound were obtained; melting point 69°-70° C.

EXAMPLE 8

(all-E)-1-(4-Carbomethoxyphenyl)-4-methyl-6-(2,6,6-trimethyl-1-cyclohexen-1-yl)-1,3,5-hexatriene Using a method similar to that described in Example 1, 116.8 g (0.2 mole) of β-ionylideneethyltriphenylphosphonium hydrogen sulfate and 32.8 g (0.25 mole) of terephthalic acid aldehyde methyl ester were converted to 113 g of crude product, which was further processed as follows. The crude product discharged was taken up in toluene, heptane was added, and the solid formed at room temperature was filtered off. The filtrate was evaporated down, the residue was dissolved in ethanol/methanol, and the solution was placed in a freezer (−20° C.). The resulting crystals were filtered off under suction and dried. 31 g of a mixture of 1 part of the title compound and 2 parts of the 1Z-isomer remained. 1 g of the title compound of melting point 77°-82° C. was obtained by repeated recrystallization from ethanol/methanol mixtures with increasing amounts of methanol (ethanol/methanol ratio=1:4 for the final crystallization).

We claim:

1. A substituted hexatriene derivative of the formula I

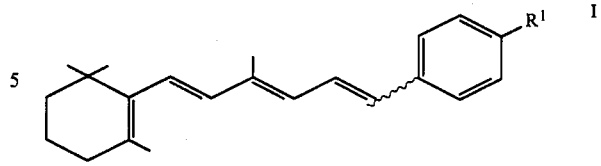

wherein
R$^1$ is tetrazolyl or —COR$^5$, where
R$^5$ is —OR$^6$, where
R$^6$ is hydrogen or C$_{1-6}$-alkyl and their physiologically tolerated salts.

2. The compounds according to claim 1 in the all-E form.

3. (all-E)-1-(4-Carboxyphenyl)-4-methyl-6-(2,6,6-trimethyl-1-cyclohexen-1-yl)-1,3,5-hexatriene.

4. (all-E)-1-[4-Tetrazol-5-yl)-phenyl]-4-methyl-6-(2,6,6-trimethyl-1-cyclohexen-1-yl)-1,3,5-hexatriene.

5. A substituted hexatriene derivative as defined in claim 1, wherein R$^1$ is —COR$^5$, R$^5$ is —OR$^6$ and R$^6$ is C$_1$-C$_6$-alkyl.

6. The compounds of claim 5 in the all-E form.

7. A therapeutic composition for pharmaceutical use comprising a pharmaceutically acceptable carrier and an effective amount of a compound of claim 1 as the active ingredient.

8. The method of treating acne which comprises administering either topically or systemically an effective amount of compound of claim 1.

9. The method of treating psoriasis which comprises: administering either topically or systemically an effective amount of a compound of claim 1.

10. The method of treating acne which comprises: administering either topically or systemically an effective amount of the compound of claim 3.

11. The method of treating psoriasis which comprises: administering either topically or systemically an effective amount of the compound of claim 3.

* * * * *